(12) United States Patent
Badiger et al.

(10) Patent No.: US 7,572,863 B2
(45) Date of Patent: Aug. 11, 2009

(54) HYDROPHOBICALLY MODIFIED POLY(ACRYLIC ACID) [PAA] AND PROCESS OF PREPARATION THEREOF

(75) Inventors: Manohar Virupax Badiger, Maharashtra (IN); Prakash Purushot Wadgaonkar, Maharashtra (IN); Ashish Kishori Lele, Maharashtra (IN); Aarti Subhash Shedge, Maharashtra (IN); Dominque Hourdet, Paris (FR); Patrick Perrin, Paris (FR); Christophe Chassenieux, Paris (FR)

(73) Assignees: Countil of Scientific and Industrial Research, New Delhi (IN); Ecole Superieur de Physique et Chimie Industrielles de la Ville de Paris (ESPCI), Paris (FR)

( * ) Notice: Subject to any disclaimer, the term of this patent is extended or adjusted under 35 U.S.C. 154(b) by 266 days.

(21) Appl. No.: 11/218,723

(22) Filed: Sep. 6, 2005

(65) Prior Publication Data

US 2006/0142501 A1   Jun. 29, 2006

(51) Int. Cl.
*C08F 8/14*  (2006.01)
*C08F 20/06* (2006.01)
*C08F 20/18* (2006.01)

(52) U.S. Cl. ............... 525/330.1; 525/329.7; 525/330.3; 525/384; 526/317.1

(58) Field of Classification Search ............. 525/329.7, 525/330.1, 330.3, 384; 526/317.1
See application file for complete search history.

(56) References Cited

U.S. PATENT DOCUMENTS 6,355,727 B1 *  3/2002  Andrist et al. ................. 525/75

* cited by examiner

*Primary Examiner*—Roberto Rábago
(74) *Attorney, Agent, or Firm*—Nixon & Vanderhye P.C.

(57) ABSTRACT

The present invention relates to the development of hydrophobically modified polymers [HMPs], which have emerged as promising materials in diverse fields such as paints, cosmetics, oils, food and textiles. They are used as thickeners in these applications. In our study, the hydrophobic modification on PAA was performed using hydrophobic compounds obtained from naturally occurring materials such as Cashew Nut Shell Liquid, [CNSL]. The DCCI coupling method was chosen for the hydrophobic modification of PAA. A series of hydrophobically modified PAAs were synthesized with different degrees of hydrophobic contents and were characterized by solution rheology.

13 Claims, No Drawings

HYDROPHOBICALLY MODIFIED POLY(ACRYLIC ACID) [PAA] AND PROCESS OF PREPARATION THEREOF

FIELD OF INVENTION

The present invention relates to a hydrophobically modified poly (acrylic acid) (PAA) of the formula (1)

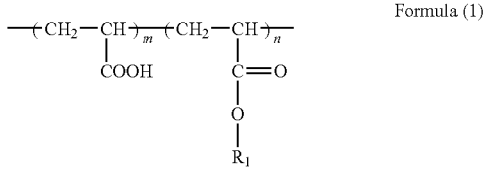

Formula (1)

wherein $R_1$ is $C_1$-$C_{18}$ alkyl group, $C_6H_5$ with alkyl group or any hydrophobic group. m and n can vary depending on the molecular weights. The incorporation of hydrophobic groups is between 0 1-4.0 mol % based on the backbone PAA.

The modified PAA polymers of the present invention are prepared by a coupling reaction between carboxyl groups of PAA and the hydrophobic compounds (formula 2 and 3) obtained from renewable resources such as cashew nut shell liquid (CNSL), as given below,

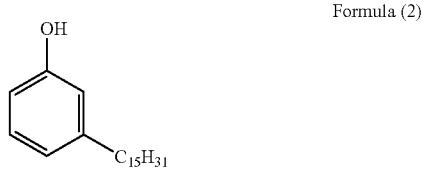

Formula (2)

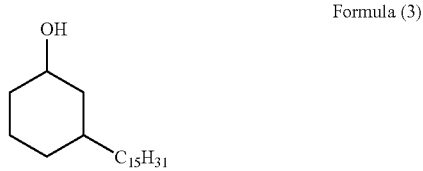

Formula (3)

BACKGROUND OF THE INVENTION

One of the exciting developments in the area of high technology in the recent past concerns hydrophobically modified polymers (HMPs) which are able to self associate in aqueous media and form reversible networks with spectacular viscoelastic properties such as enhanced viscosification efficiency, shear thickening property, shear and salt stability. Therefore, they find extensive applications in enhanced oil recovery, cosmetic lotions, paints, coatings, food additives and pharmaceuticals. These polymers consist of a hydrophilic backbone with a small number of hydrophobic groups dispersed along the chain or terminally situated on the chain. There are two ways to incorporate the hydrophobic moities in the water-soluble polymer i.e. the direct copolymerization of hydrophobic monomers with water-soluble monomers or the post modification method using water-soluble polymers. (Water-Soluble Polymers: Synthesis, Solution Properties and Applications, Edts. S. W. Shalaby, C. L. McCormick, G. B. Butler, ACS Symp Ser. 467, Washington, 1991; Polymers in Aqueous Media: Performance Through associations Edt. J. E. Glass, Adv Chem ser. 223, ACS, Washington, 1989; Macromolecular Complexes in Chemistry and Biology Edts. P. Dubin, R. M. Davies, D. N. Schultz, C. Thies, Springer Verlag, Berlin 1994; L. M. Landoll, U.S. Pat. No. 4,228,277, 1980)

Various molecular architectures such as random, graft, block and hydrophobically end-capped polymers have been envisaged in designing hydrophobically modified polymers. (Iliopoulos et.al., Langmuir 7, 617, 1991; J. E. Glass et.al. Macromolecules, 26, 5149, 1993; Ma and Cooper, Macromolecules, 34, 3294, 2001, Arotcarena et.al., JACS, 124, 3787, 2002, McCormick et.al., Polymer, 29, 731, 1988; Hill et.al., Macromolecules, 26, 4521, 1993)

Although, there are fast expanding academic studies on associating polymers, their industrial development has not really taken place and only a small number of polymers are commercially available. Therefore, there is a need to develop newer HMPs for specific end applications.

Hydrophobic association plays a dominant role in governing co-operative aggregation process in aqueous environment. For example, surfactant self assembly, protein folding, formation of biological membranes and molecular recognition.

The hydrophobic compounds constitute alkyl substituted phenols and cyclohexanols. The alkyl substituted phenols can be derived from renewable resources such as, CNSL which is available abundantly in India and is inexpensive.

Hydrophobically end-capped polymers contain hydrophobic moieties having 8-18 C-atoms (alkyl, perfluoroalkyl) or aromatic groups. The main representatives are the Hydrophobically modified Ethoxylated URethanes (HEUR), which are obtained by coupling poly(ethylene glycol) and alkylamines with diisocyanates. These are one of the earlier HMPs prepared and have undergone major industrial development. HEURs have been widely studied from a fundamental point of view as model associative thickeners. HEUR polymers offer the greatest variation in architectural design of any hydrophobically modified polymers. In the case of graft copolymers, the hydrophobic groups such as alkyl, perfluoroalkyl or aromatic rings are distributed along the hydrophilic backbone chains. For example, the modifications of polysaccharides is generally performed through the functionalization of hydroxyl groups with alkyl substituents. Number of such systems like HM-pullulan (Akiyoshi, et.al Chemistry Lett, 1727, 1992), guar (Aubry and Moan, J. Rheol, 38, 1681, 1994), alginates (Sinquin et.al., Langmuir, 9, 3394, 1993), and cellulose have been reported in the literature. In the case of synthetic polymers, polymers based on polyacrylamide, polyacrylic acid, polymethacrylic acid have been reported. Some graft copolymers namely, Hydrophobically modified Alkali Swellable/Soluble Emulsion were developed at Union Carbide Corporation, USA and were prepared by emulsion copolymerization technique using methacrylic acid, ethyl acrylate and a hydrophobic comonomer. Tirtatmadja, et.al., (Macromolecules, 30, 3271, 1994) and Wang et. al., (Polym. Bull. 20, 577 1988) have reported the associating polymers based on the grafting of alkyl amines on the PAA backbone chain using Dicyclohexyl carbodiimide (DCCI), coupling agent in an aprotic solvent. The solution properties of these polymers were found to depend on the degree of hydrophobic content and the alkyl chain length. The influence of surfactants and salts on the viscometric behaviour of the modified PAA solutions were also reported. Other HMPs based on modified PAA were also reported. During the same time, the concept of thermoassociating polymers was evolved. This concept, based on the switch properties of macromolecular side chains, which is characterized by a lower critical solution temperature (LCST), was generalized with a large set of copolymers designed with thermosensitive side chains such as PEO, PPO, PNIPAM grafted onto water soluble backbones such as PAA, PAM and other polyelectrolytes (Maroy P., Hourdet D., L'Alloret and Audebert R., Eur. Patent 0 583 814 A1 1993; Durand A., Herve M., Hourdet D., in "Stimuli-Responsive Water Soluble and Amphiphilic Polymers" C. L. McCormick Ed., ACS Symposium Series 780, Chapter 11, 181-207, 2000). These polymers were studied in aqueous solutions with various added co-solutes such as salts, neutral species and anionic surfactants. In aqueous solution these polymers provide an enhancement of the viscosity on heating, the extent of which can be controlled by polymer concentration, grafting ratios, salt concentrations etc. Along the same lines, polyaspartic acid modification has also been reported (Polym. Bull. 44, 385, 2000, Polym. Bull. 45, 39, 2000). An excellent review on the hydrophobic association in perfluorocarbon containing water-soluble polymers has been reported. (Hogen-Esch and Amis, Trends in Polym Sci, 3, 98, 1995). Synthesis of fluorocarbon modified poly(acrylic acid) in supercritical $CO_2$ has been reported (Polymer, 43, 6357, 2002). In aqueous solution and above a certain threshold polymer concentrations, the hydrophobic groups form interchain aggregates that stabilize a transient network. As a result, the viscosity enhancement is observed. Addition of surfactants and salts to the aqueous solutions of HMPs further enhance their thickening properties. (Iliopoulos et.al., Langmuir, 617, 1991; Zhuang et.al., 43, 2075, 2002; Magny et.al., Polymer, 33, 3151, 1992; Morishima, Prog. Polym. Sci., 15, 949, 1990; Ringsdorf et.al., Macromolecules, 25, 7306, 1992).

OBJECTS OF THE INVENTION

The main objective of the present invention is to provide novel hydrophobically modified polymers using the combination of synthetic polymers and hydrophobic compounds derived from renewable resources and a process for preparation thereof.

Another objective is to study various physico-chemical aspects, which include coordinated studies of self assembly, interactions with salt and surfactants and viscoelastic properties.

Still another object is to provide a simple and yet elegant method for the preparation of hydrophobically modified polymer using hydrophobic compounds obtained from renewable resource materials. In aqueous solutions these systems self organize forming hydrophobic clusters embedded in a sea of hydrophilic chains. This results in a transient network structure, which enhances the viscoelastic properties of the solution.

Yet another object of the present invention is to provide an understanding of the associative properties of HMPs in solutions Yet another object of the present invention is to synthesize hydrophobically modified PAA with varying degree of hydrophobic contents.

Still another object is to study the influence of environmental parameters (pH, temperature, salt, surfactants, etc.) on the solution properties of HMPs.

SUMMARY OF INVENTION

The present invention relates to a class of hydrophobically modified polymers with different molecular architectures. Still more particularly, the present invention provides hydrophobically modified graft-co-PAA. Hydrophobically modified polymers have emerged as promising materials lately due to their unusual rheological properties, They find applications in various areas, which include cosmetic lotions, paints, coatings, textiles, food and pharmaceuticals.

Accordingly, the present invention provides hydrophobically modified polymers having formula (1)

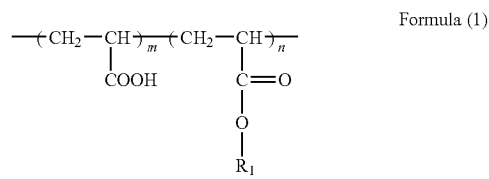

Formula (1)

wherein, $R_1$ is $C_6 H_5$-$C_{15}$ (alkyl phenyl) and 'm' and 'n' vary depending on the molecular weights.

In one embodiment the molecular weight of the backbone poly(acrylic acid) is in the range of 100,000 to 250,000 daltons.

In another embodiment of the invention the hydrophobic content is in the range of 0.1-4.0 mol % (w/w).

The present invention also provides a process for the preparation of a hydrophobically modified PAA having formula (1)

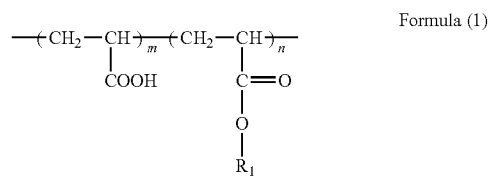

Formula (1)

wherein, $R_1$ is $C_6 H_5$-$C_{15}$ (alkyl phenyl) and 'm' and 'n' vary depending on molecular weights, the process comprising coupling of hydrophobic compounds (formula 2 and 3) with PAA

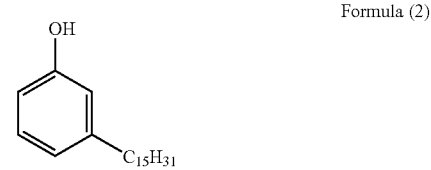

Formula (2)

Formula (3)

using a coupling agent in an aprotic solvent, allowing the reaction to continue, isolating and then drying product to obtain the pure hydrophobically modified PAA (HMP).

In one embodiment of the invention, the reaction is allowed to continue for a period in the range of 12-24 hrs. and at a temperature of about 60° C.

In another embodiment of the invention, the product is isolated by precipitating in a non-solvent and is then vacuum dried at 40° C.

In another embodiment of the invention, the water-soluble polymer used for the preparation of HMP is selected from the group consisting of poly (acrylic acid), poly(methacrylic acid), poly(aspartic acid), copolymer of poly(acrylic acid) and poly(2-acrylamido 2-methyl propane sulfonic acid).

In another embodiment of the invention the hydrophobic compounds consist of 3-penta decyl phenol [3-PDP] and an alkyl amine.

In another embodiment of the invention, the aprotic solvent is selected from the group consisting of N-methyl pyrrolidone, dimethyl formamide and 1-4 dioxane.

In another embodiment of the invention, the coupling agent is selected from the group consisting of DCCI, 1-cyclohexyl 3-2-morpholino ethyl carbodiimide metho-p-toluene sulfonate (CMC) and 1-ethyl-3-(3-dimethylamino propyl) carbodiimide (EDC).

In another embodiment of the invention, the reaction is carried out in the presence of a catalyst/accelerator consisting of DMAP to enhance the reaction rate.

In another embodiment the hydrophobic content in the polymer is in the range of 0.1 to 4.0 mol %

In another embodiment of the invention, the non-solvent used to precipitate HMP is selected from the group consisting of methanol, ethanol and isopropanol.

In another embodiment of the invention, the hydrophobic modification is carried out at a temperature in the range of 50-80° C.

DETAILED DESCRIPTION OF THE INVENTION

The hydrophobically modified polymer of the invention shows improved solution properties such as enhanced viscosification, shear and temperature stability. Although, there are a few reports on modified PAA, this is the first report on the modification of PAA with hydrophobic compounds of formula (2) and (3) above obtained from the renewable resources, CNSL (cashew nut shell liquid).

The present invention provides for the synthesis of hydrophobically modified poly (acrylic acid) with 3-pentadeyl phenol derived from the cashew nut shell liquid (CNSL), a renewable resource material, available in abundance in India. These modified polymers show excellent solution properties compared to the unmodified precursor. Because of their enhanced properties, they have potential application in EOR, cosmetic lotions and creams.

The present invention is the first attempt to modify PAA with the hydrophobic compounds, which are obtained from renewable resource materials.

The present invention relates to the hydrophobically modified poly(acrylic acid) and preparation thereof. The hydrophobic compounds used in this study were derived from a renewable resource material viz CNSL. The approach described herein consists of post-polymerization coupling of hydrophobic groups onto poly(acrylic acid). Therefore, the hydrophobic groups are randomly dispersed along the polymer backbone chain. The present invention involves a coupling reaction of alkyl phenol with a carboxylic groups of PAA in an aprotic solvent such as NMP, 1-4 dioxane etc. in the presence of dicyclohexyl dicarbodiimide (DCCI).

Poly acrylic acid was chosen as the backbone chain in the present invention due to several reasons. The chemistry of PAA is more versatile and the coupling reactions can be carried out in both aqueous and organic media. Furthermore, under the ionized form, PAA is highly soluble in water even with hydrophobic content of as high as 20 mol %. Incorporation of hydrophobic groups onto polymers containing carboxylic groups can be in principle be done by acid chloride reactions. However, the handling of acid chloride of polymers is very difficult and moreover these reactions are very sensitive to the moisture. Alternatively, DCCI coupling reactions are well established for amines, alcohols and acids. Therefore, in the present investigations, DCCI coupling reaction was used for the modification of PAA. DCCI is found to be an efficient reagent for such coupling reactions. A base such as dimethyl amino pyridine (DMAP) is used as a catalyst/accelerator in these reactions. Additionally, the side product is dicyclohexyl urea in these reactions, which can be easily removed from the product since it is insoluble in most aprotic solvents that are used for such coupling reactions.

We have found that coupling reaction between 3-PDP and PAA is more efficient in aprotic solvent, 1,4 dioxane. Many of the water-soluble polymers such as polyethylene glycol, polyvinyl alcohol, poly(acrylic acid), polyamide, poly(aspartic acid), polysaccharides (EPEC, HPC) etc. can be hydrophobically modified by incorporating hydrophobic groups. The hydrophobic content in these polymers is less than 3-4 mol % and above this, the polymer becomes insoluble in water due to the dominance of hydrophobic of the polymer The term hydrophobic modification means the incorporation of hydrophobic groups such as long chain alkyl [$C_8$-$C_{18}$] groups (octyl, dodecyl, hexadecyl, octadecyl amines etc), nonyl phenols, long chain terminal epoxides. Various molecular architectures such as random, block, graft copolymers, end-capped polymers and interpolymer complexations have been envisaged for designing hydrophobically modified polymers.

The hydrophobically modified polymers obtained essentially satisfies the formula (1)

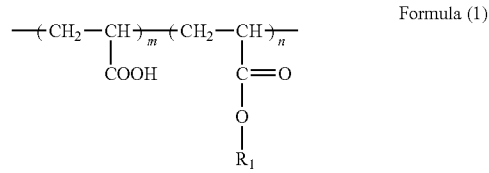

Formula (1)

wherein, $R_1$ is $C_6H_5$-$C_{15}$ (alkyl phenyl) the 'm' and 'n' vary depending on the molecular weights.

The molecular weight of the backbone poly(acrylic acid) ranged from 100,000 to 250,000 daltons and the hydrophobic content varies from 0.1-4.0 mol % (w/w).

The process for preparation of the HMP of formula (1) essentially comprised coupling of hydrophobic compounds (formula 2 and 3) using DCCI reagent in an aprotic solvent, allowing the reaction for a period of 12-24 hrs. at 60° C., isolating the product by precipitating in a non-solvent, vacuum drying the product at 40° C. to obtain the pure HMP.

The water-soluble polymer used for the preparation of HMPs can be poly (acrylic acid), poly(methacrylic acid), poly(aspartic acid), copolymer of poly(acrylic acid) and the poly(2-acrylamido 2-methyl propane sulfonic acid). The hydrophobic compounds can be 3-penta decyl phenol [3-PDP], alkyl amines. The aprotic solvents used for hydrophobic modifications are preferably N-methyl pyrrolidone, dimethyl formamide or 1-4 dioxane.

The coupling agent is selected from compounds such as DCCI, 1-cyclohexyl 3-2-morpholino ethyl carbodiimide metho-p-toluene sulfonate (CMC), 1-ethyl-3-(3-dimethylamino propyl) carbodiimide (EDC). A catalyst/accelerator, DMAP can be used to enhance the reaction rate.

The hydrophobic content in these polymers ranges from 0.1 to 4.0 mol %.

The non-solvent used to precipitate the HMP may be methanol, ethanol, isopropanol. The hydrophobic modification is preferably carried out in the temperature range of 50-80° C.

The hydrophobically modified polymers are useful for applications in health care products such as lotions and creams, etc. The HMPs exhibit enhanced/improved solution properties and are more stable towards temperature, salts and shear as compared to their unmodified precursors. It is believed that the present invention is the first report on the hydrophobic modification of PAA by using hydrophobic compound, which is derived from the renewable resources. The observed enhanced solution properties of HMPs are attributed to association of hydrophobic groups dispersed along the backbone chain.

The synthesis of HMPs of the invention is described below with reference to illustrative examples, which should not be constructed to limit the scope of the present invention in any manner.

EXAMPLE 1

This example describes the process for the preparation of hydrophobically modified PAA using 3-penta decyl phenol (3-PDP), which is derived from CNSL.

Hydrophobically modified PAA was synthesized by the coupling reaction of alkyl phenol (3-PDP) on carboxyl groups of PAA (PAA-250 Aldrich, MW-250, 000) in an aprotic solvent, 1,4 dioxane, in the presence of DCCI.

PAA-250 (0.695 mol) was dissolved over 12 h in 1,4 dioxane (175 ml) at 60° C. 3-PDP (0.0138 mols) and DCCI (0.00694 mols) were separately dissolved in 1,4 dioxane (25 ml) each and added drop wise (over 15 min) to PAA-250 solution. The reaction was carried out at 60° C. for 24 h. The product was dissolved in water and neutralized with sodium bicarbonate (10 wt %). The neutralized polymer was precipitated in methanol. Washing with hot dioxane and methanol, purified the polymer. Finally the product was dried under vacuum at room temperature. Hydrophobically modified PAAs with different contents of hydrophobic compounds were prepared using the above-mentioned procedure. The stoichiometry of the reaction is given in table 1

TABLE 1

Stoichiometry of reactions between PAA and hydrophobe

| PAA (Mol) | Mol (%) 3-PDP | 3-PDP (g) | DCC (g) | DMAP (g) | Dioxane (ml) |
|---|---|---|---|---|---|
| 0.069 | 0.5 | 0.00047 | 0.0023 | 0.0023 | 225 |
| 0.069 | 1 | 0.00069 | 0.0034 | 0.0034 | 225 |
| 0.069 | 2 | 0.00138 | 0.0069 | 0.0069 | 225 |

EXAMPLE 2

This example describes the Rheological characterizations of the hydrophobically modified PAA (2.0 mol % modification). In order to evaluate the solution properties of the modified PAA, the steady shear experiments were performed on 2.0 wt % solution of the unmodified and the hydrophobically modified PAA using a strain controlled rheometer (ARES, Rheometric scientific). Cup and bob, parallel plate, cone and plate geometries were used depending on the consistency of the solutions. Steady shear stress and corresponding viscosities were measured at 30, 40, and 60° C.

The comparative study between the steady shear rheology of the unmodified and the hydrophobically modified poly (acrylic acid) solutions at 30° C. and 40° C. shows that the poly(acrylic acid) solutions exhibit a Newtonian behaviour, i.e., the shear stress increases linearly with shear rate and the shear viscosity (~7 cP) is constant over the range of shear rates probed. The low viscosity and the Newtonian behaviour are indicative of the fact that the solution is probably dilute (i.e., there are no entanglement effects). The viscosity decreases with increasing temperature as expected. In contrast, the hydrophobically modified poly(acrylic acid) shows very high low-shear viscosity (~50,000 times higher than that of the unmodified poly(acrylic acid) solution under the similar conditions).

The hydrophobically modified polymer solutions also show shear thinning behaviour.

We claim:

1. Hydrophobically modified polymer (HMP) having formula (1)

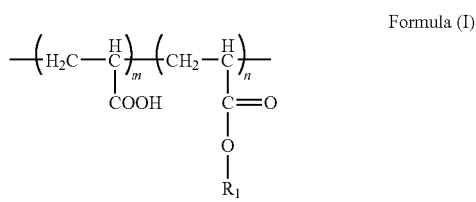

Formula (I)

with a poly (acrylic acid) backbone chain, wherein, $R_1$ is $C_6H_4$—$C_{15}H_{31}$

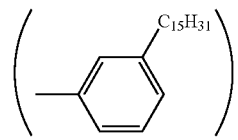

or $C_6H_{10}$—$C_{15}H_{31}$

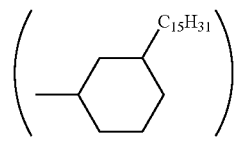

where 'm' and 'n' vary depending on molecular weights.

2. A polymer as claimed in claim 1 wherein the molecular weight of the backbone poly(acrylic acid) is in the range of 100,000 daltons to 250,000 daltons.

3. A polymer as claimed in claim 1 wherein the hydrophobic content is in the range of 0.1 -4.0 mol %.

4. A process for the preparation of a hydrophobically modified PAA having formula (1)

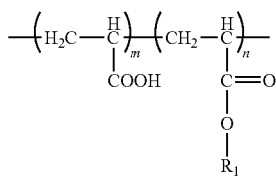

Formula (I)

wherein, R1 is $C_6H_4$—$C_{15}$—$H_{31}$ or $C_6H_{10}$—$C_{15}H_{31}$ and 'm' and 'n' vary depending on molecular weights, the process comprising coupling of hydrophobic compounds (formula 2 and 3) with PAA

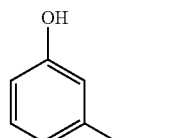

Formula (2)

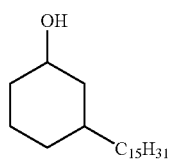

Formula (3)

using a coupling agent in an aprotic solvent, allowing the reaction to continue, isolating and then drying product obtained to obtain the pure hydrophobically modified PAA (HMP).

5. A process as claimed in claim 4 wherein the reaction is allowed to continue for a period in the range of 12-24 hours and at a temperature of about 60° C.

6. A process as claimed in claim 4 wherein the product is isolated by precipitating in a non-solvent and is then vacuum dried at 40° C.

7. A process as claimed in claim 4 wherein the polymer used for the preparation of HMP is poly(acrylic acid).

8. A process as claimed in claim 4 wherein the aprotic solvent is selected from the group consisting of N-methyl pyrrolidone, dimethyl formamide and 1-4 dioxane.

9. A process as claimed in claim 4 wherein the coupling agent is selected from the group consisting of Dicylohexyl-dicarbodiimide (DCCI), 1-cyclohexyl 3-2-morpholino ethyl carbodiimide metho-p-toluene sulfonate (CMC) and 1-ethyl-3-(3-dimethyl amino propyl) carbodiimide (EDC).

10. A process as claimed in claim 4 wherein the reaction is carried out in the presence of a catalyst/accelerator consisting of DMAP to enhance the reaction rate.

11. A process as claimed in claim 4 wherein the hydrophobic content in the polymer is in the range of 0.1 to 4.0 mol %.

12. A process as claimed in claim 4 wherein the HMP is precipitated using a non-solvent selected from the group consisting of methanol, ethanol and isopropanol.

13. A process as claimed in claim 4 wherein the hydrophobic modification is carried out at a temperature in the range of 50-80° C.

* * * * *